United States Patent
Sasai et al.

(10) Patent No.: US 7,923,246 B2
(45) Date of Patent: Apr. 12, 2011

(54) METHOD OF CULTURING EMBRYONIC STEM CELLS WITH THE USE OF AMNIOTIC MEMBRANE-ORIGIN FACTOR

(75) Inventors: Yoshiki Sasai, Kobe (JP); Morio Ueno, Kobe (JP); Shigeru Kinoshita, Kyoto (JP)

(73) Assignee: Riken, Wako-shi (JP)

( * ) Notice: Subject to any disclaimer, the term of this patent is extended or adjusted under 35 U.S.C. 154(b) by 173 days.

(21) Appl. No.: 11/569,414

(22) PCT Filed: May 27, 2005

(86) PCT No.: PCT/JP2005/010201
§ 371 (c)(1),
(2), (4) Date: Jan. 10, 2007

(87) PCT Pub. No.: WO2005/116191
PCT Pub. Date: Dec. 8, 2005

(65) Prior Publication Data
US 2007/0178587 A1     Aug. 2, 2007

(30) Foreign Application Priority Data

May 27, 2004   (JP) ................................ 2004-158421

(51) Int. Cl.
*C12N 5/00* (2006.01)
*C12N 5/02* (2006.01)
*C12N 5/071* (2010.01)

(52) U.S. Cl. .......................... 435/377; 435/366; 435/368

(58) Field of Classification Search .................. 435/377, 435/366, 368
See application file for complete search history.

(56) References Cited

U.S. PATENT DOCUMENTS

| | | |
|---|---|---|
| 2002/0151056 A1 | 10/2002 | Sasai et al. |
| 2005/0214259 A1 | 9/2005 | Sano et al. |
| 2005/0287126 A1 | 12/2005 | Nakamura et al. |
| 2006/0281179 A1 | 12/2006 | Sasai et al. |

FOREIGN PATENT DOCUMENTS

| | | |
|---|---|---|
| EP | 1 302 533 A1 | 4/2003 |
| JP | 2004-024852 A | 1/2004 |
| JP | 2005-137337 A | 6/2005 |
| WO | WO 01/88100 A1 | 11/2001 |
| WO | WO 03/042384 A1 | 5/2003 |
| WO | WO 03/043542 A1 | 5/2003 |

OTHER PUBLICATIONS

Ginnis et al. Developmental Biology, 269: 360-380, 2004.*
Ferletta et al. Mol. Cancer Res. 5(9): 891-897, 2007.*
"NCAM" from Wikipedia, accessed online on Apr. 3, 2009, www.en.wikipedia.com.*
"Tyrosine Hydroxylase" from Wikipedia, accessed online on Apr. 3, 2009, www.en.wikipedia.com.*
"Catecholamine" from Wikipedia, accessed online on Apr. 3, 2009, www.en.wikipedia.com.*
Verfaillie et al. Hematology, pp. 369-381, 2002.*
Hoffman et al. Nature Biotech., 23(6): 699-708, 2005.*
Dhara et al. J. Cell Biochem., 105: 633-640, 2008.*
Bain et al., *Developmental Biology*, 168: 342-357 (1995).
Finley et al., *The Journal of Neuroscience*, 16(3): 1056-1065 (Feb. 1, 1996).
Kawasaki et al., *Neuron*, 28: 31-40 (Oct. 2000).
Kawasaki et al., *Proc. Natl. Acad. Sci.*, 99(3): 1580-1585 (Feb. 5, 2002).
Lee et al., *Nature Biotechnology*, 18: 675-679 (Jun. 2000).
Miyamoto Kanji, *MRS-J News*, 6(1): 2-3 (Jul. 2004) (with English translation).
Miyamoto et al., *Stem Cells*, 22: 433-440 (2004).
Mizuseki et al., *Proc. Natl. Acad. Sci.*, 100(10): 5828-5833 (May 13, 2003).
Ooto et al., *Investigative Ophthalmology & Visual Science*, 44(6): 2689-2693 (Jun. 2003).
Pera et al., *Genes & Dev.*, 17: 3023-3028 (2003).
Sasai et al., *Nature*, 376: 333-337 (Jul. 27, 1995).
Yamada et al., *Biochemical and Biophysical Research Communications*, 199(2): 552-563 (Mar. 15, 1994).
Ying et al., *Nature Biotechnology*, 21: 183-186 (Feb. 2003).
Koizumi et al., *Current Eye Research*, 20(3): 173-177 (2000).
Schuldiner et al., *Proc. Natl. Acad. Sci.* U.S.A., 97(21): 11307-11312 (Oct. 10, 2000).
Ueno et al., *Proc. Natl. Acad. Sci.* U.S.A., 103(25): 9554-9559 (Jun. 20, 2006).
Xu et al., *Stem Cells*, 23(3): 315-323 (Mar. 2005).
Zhang et al., *Nature Biotechnology*, 19(12): 1129-1133 (Dec. 2001).

* cited by examiner

*Primary Examiner* — Thaian N Ton
(74) *Attorney, Agent, or Firm* — Leydig, Voit & Mayer, Ltd.

(57) ABSTRACT

The present invention provides a clinically applicable method of inducing differentiation of the embryonic stem cells. Specifically, the present invention provides a method of culturing embryonic stem cells, which comprises culturing embryonic stem cells in the presence of an amnion-derived factor, a cell culture obtained by the culture method, and a culture agent/culture kit of embryonic stem cells comprising an amnion-derived factor. The present invention also provides a method of screening an amnion-derived factor having an activity useful for culturing embryonic stem cells with the activity as an index, and an amniocyte-derived factor obtained by the screening method. Furthermore, the present invention provides a method of preparing amniocytes useful for culturing embryonic stem cells, amniocytes obtained by the preparation method, and the like.

5 Claims, No Drawings

METHOD OF CULTURING EMBRYONIC STEM CELLS WITH THE USE OF AMNIOTIC MEMBRANE-ORIGIN FACTOR

TECHNICAL FIELD

The present invention relates to a method of culturing embryonic stem cells using an amnion-derived factor, a culture agent/culture kit of embryonic stem cells comprising an amnion-derived factor, a screening method for an amnion-derived factor useful for culturing embryonic stem cells, a method of preparing amniocytes useful for culturing embryonic stem cells and the like.

BACKGROUND ART

Embryonic stem cells are promising candidates for a source of cells for cell transplantation for Parkinson's disease and diabetes mellitus. However, even embryonic stem cells derived from mice, humans and other primates require the coexistence with mouse-derived feeder cells (stromal cells) in their culture and differentiation induction, and this represents a major barrier against their clinical applications.

Recently, the present inventors developed a method of inducing the differentiation of mouse and monkey embryonic stem cells into neurons at high efficiency (SDIA method) (see pamphlet for International Patent Publication No. WO01/088100; pamphlet for International Patent Publication No. WO03/042384; Kawasaki et al., Neuron, vol, 28, p. 31-40 (2000); Kawasaki et al., Proceedings of the National Academy of Sciences of the USA, vol, 99, p. 1580-1585 (2002); Mizuseki et al., Proceedings of the National Academy of Sciences of the United States of America, vol, 10, p. 5828-5833 (2003); Ooto et al., Invest. Ophthalmol. Vis. Sci., vol, 44, p. 2689-2693 (2003)). Using this method, the present inventors succeeded in producing in vitro dopamine-secreting neurons, which are expected to be applied to transplantation therapy for Parkinson's disease, and motor neurons, which are speculated to be applied to treatment for amyotrophic lateral sclerosis, from mouse and monkey embryonic stem cells (see pamphlet for International Patent Publication No. WO01/088100; pamphlet for International Patent Publication No. WO03/042384; Kawasaki et al., Neuron, vol, 28, p. 31-40 (2000); Kawasaki et al., Proceedings of the National Academy of Sciences of the USA, vol, 99, p. 1580-1585 (2002); Mizuseki et al., Proceedings of the National Academy of Sciences of the United States of America, vol, 100, p. 5828-5833 (2003); Ooto et al., Invest. Ophthalmol. Vis. Sci., vol, 44, p. 2689-2693 (2003)).

However, considering human applications in a long viewpoint, one of the major problems with this SDIA method is the necessity for coculture with embryonic stem cells during differentiation induction of mouse bone marrow-derived stromal cells (PA6 cells). To date, differentiation of embryonic stem cells into nerves has not efficiently been performed in the absence of stromal cells such as PA6 cells. However, because of coculture with mouse-derived cells, even neurons produced using human embryonic stem cells involve the same level of risk as heterologous transplantation with regard to the safety of transplantation (in terms of contamination with heterologous cells and pathogens, and the like), thus posing a major barrier against their clinical applications.

Also, as another differentiation-inducing method for embryonic stem cells, a method using retinoic acid is known (see Bain et al., Dev. Biol., vol, 168, p. 342-357 (1995)), but this method has been problematic in that the dopamine nerve differentiation induction rate is very low. Also, although a method of selection culture of nerve precursor cells differentiated from aggregation cultured ES cells using a selection medium has also been known (see Lee et al., Nature Biotech., vol, 18, p. 675-679 (2000)), this method has been problematic in that it takes a time doubling to tripling that for the SDIA method.

Against this background, there has been a strong demand for a method that assures the safety of transplantation of cells obtained by culturing embryonic stem cells and also enables efficient induction of differentiation of embryonic stem cells into particular functional cells, for example, neurons.

DISCLOSURE OF THE INVENTION

Accordingly, it is an object of the present invention to develop a more practical method enabling clinical applications of cells obtained by culturing, for example, differentiation-inducing, embryonic stem cells.

The present inventors conducted diligent investigations to solve the above-described problems, and found that a factor present in the amnion is useful for culturing, for example, differentiation inducing and growing, embryonic stem cells. Because the amnion has advantages, such as unlikelihood of graft rejection reactions, easy availability, and much experience with clinical use and hence high safety, it is thought to be very useful as a culture agent of embryonic stem cells. Based on the finding above, the present inventors had the idea to culture embryonic stem cells in the presence of an amnion-derived factor, and completed the present invention. Accordingly, the present invention is as follows:

(1) A method of culturing embryonic stem cells, which comprises culturing the embryonic stem cells in the presence of an amnion-derived factor;
(2) the method (1) above, wherein the embryonic stem cells are cultured in a serum-free medium;
(3) the method (1) or (2) above, wherein both the amnion-derived factor and embryonic stem cells are derived from the same mammalian species;
(4) the method (3) above, wherein the amnion-derived factor is derived from a human;
(5) the method (1) above, which is a method of inducing differentiation of the embryonic stem cells;
(6) the method (5) above, wherein differentiation of the embryonic stem cells into nervous system cells is induced;
(7) the method (6) above, wherein the nervous system cells are catecholamine-secreting neurons;
(8) the method (6) above, wherein the nervous system cells are tyrosine hydroxylase-positive cells;
(9) the method (1) or (2) above, which is a method of growing the embryonic stem cells;
(10) the method (1) above, wherein the amnion-derived factor is provided in the form of cell-free tissue;
(11) a cell culture that can be obtained by any of the methods (1) to (10) above;
(12) a method of screening an amnion-derived factor having differentiation-inducing activity of the embryonic stem cells, with said activity as an index;
(13) the method (11) above, wherein the differentiation-inducing activity is activity to induce the differentiation of the embryonic stem cells into nervous system cells;
(14) a method of screening an amnion-derived factor having growth activity of the embryonic stem cells, with said activity as an index;
(15) an amnion-derived factor that can be obtained by the method (12) or (14) above;
(16) an agent of culturing embryonic stem cells, which comprises an amnion-derived factor;

(17) the agent (16) above, wherein the amnion-derived factor has differentiation-inducing activity of the embryonic stem cells;
(18) the agent (17) above, wherein the differentiation-inducing activity is activity to induce the differentiation of the embryonic stem cells into nervous system cells;
(19) the agent (16) above, wherein the amnion-derived factor has growth activity of the embryonic stem cells;
(20) the agent (16) above, wherein the amnion-derived factor is derived from a human;
(21) the agent (16) or (20) above, which is in a cryopreserved form;
(22) the agent (16) or (20) above, wherein the amnion-derived factor is provided in the form of cell-free tissue;
(23) a kit of culturing embryonic stem cells, comprising the following (i) and (ii):
(i) an agent of culturing the embryonic stem cells, comprising an amnion-derived factor, and
(ii) a manual stating that the kit should be used, or can be used, for culturing the embryonic stem cells;
(24) a method of preparing amniocytes having differentiation-inducing activity of embryonic stem cells, with said activity as an index;
(25) the method (24) above, wherein the differentiation-inducing activity is activity to induce the differentiation of the embryonic stem cells into nervous system cells; and
(26) a method of preparing amniocytes having growth activity of the embryonic stem cells, with said activity as an index.

BEST MODES FOR EMBODYING THE INVENTION

The present invention provides a method of culturing embryonic stem cells, which comprises culturing embryonic stem cell in the presence of an amnion-derived factor.

"The embryonic stem cells" refers to those cells which can be cultured in vitro and have a pluripotency capable of differentiating into all cells constituting the living body.

As the embryonic stem cells, cells derived from, for example, a warm blood animal, preferably, a mammal, can be used. The mammal includes, for example, mouse, rat, guinea pig, hamster, rabbit, cat, dog, sheep, pig, cattle, goat, monkey and human.

Specifically, the embryonic stem cells used in the method of the present invention include, for example, embryonic stem cells of a mammal and the like established by culturing an early embryo before implantation (hereinafter, abbreviated as "embryonic stem cell I"), an embryonic stem cell established by culturing an early embryo produced by nuclear transplantation of the nucleus from a somatic cell (hereinafter abbreviated as "embryonic stem cell II"), and an embryonic stem cell in which a gene on the chromosome of the embryonic stem cell of the embryonic stem cell I or II is modified using a gene engineering technique (hereinafter abbreviated as "embryonic stem cell III").

More specifically, the embryonic stem cell I includes an embryonic stem cell established from an early embryo-constituting inner cell mass, an EG cell established from a primordial germ cell, a cell isolated from a cell population (e.g., primitive ectoderm) having a pluripotency of an early embryo before implantation, and a cell obtained by culturing such a cell.

The embryonic stem cell I can be prepared by culturing an early stage embryo before implantation according to the method described in a reference (Manipulating the Mouse Embryo A Laboratory Manual, Second Edition, Cold Spring Harbor Laboratory Manual (1994)).

The embryonic stem cell II can be prepared as described below, for example, by using a method reported by, e.g., Wilmut et al. (Nature, 385, 810 (1997)), Cibelli et al. (Science, 280, 1256 (1998)), Akira Iritani et al. (Protein, Nucleic Acid and Enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)) or Rideout III et al (Nature Genetics, 24, 109 (2000)).

An egg which acquired the nucleus of other somatic cell and started normal development can be obtained by starting its development using a method in which the nucleus of a mammal cell is excised, initialized (an operation to return the nucleus to such a state that it can repeat the development again) and injected into an enucleated unfertilized egg of a mammal, and then incubating the development-started egg.

As the method for initializing the nucleus of a somatic cell, several methods are known. For example, the initialization can be carried out by changing the medium for culturing a nuclear donor cell from a medium containing from 5 to 30%, preferably 10%, of fetal calf serum (e.g., M2 medium) to a poor nutrient medium containing from 0 to 1%, preferably 0.5%, of fetal calf serum and culturing the cell for a period of from 3 to 10 days, preferably 5 days, thereby to induce the cell cycle into an interphase state (G0 phase or G1 phase).

Also, the initialization can be carried out by injecting the nucleus of a nucleus donor cell into an enucleated unfertilized egg from a mammal of the same species and incubating the egg for several hours, preferably from about 1 to 6 hours.

The thus initialized nucleus becomes possible to start its development in an enucleated unfertilized egg. Several methods are known as the method for starting development of the initialized nucleus in an enucleated unfertilized egg. The development can be started by transplanting a nucleus initialized by inducing the cell cycle into an interphase state (G1 phase or G1 phase) into an enucleated unfertilized egg from a mammal of the same species, e.g., by electrofusion method to thereby activate the egg.

Development of the nucleus initialized by injecting it into an enucleated unfertilized egg from a mammal of the same species can be carried out by again transplanting it into an enucleated unfertilized egg from a mammal of the same species, for example, using a method which uses a micromanipulator, stimulating it with an egg activating factor (e.g., strontium) and then treating it with a cell division inhibitor (e.g., cytochalasin B) to suppress release of a secondary polar body. This method is suitable, for example, when the mammal is a mouse or the like.

Once an egg which started the development is obtained, the embryonic stem cell can be obtained by a known method described in, for example, Manipulating the Mouse Embryo A Laboratory Manual, Second Edition, Cold Spring Harbor Laboratory Press(1994); Gene Targeting, A Practical Approach, IRL Press at Oxford University Press (1993); Biomanual series 8 Gene Targeting, Preparation of mutant mouse using ES cell, Yodosha (1995) and the like.

The embryonic stem cell III can be prepared, for example, using homologous recombination techniques. Examples of the chromosomal gene to be modified for producing the embryonic stem cell III include genes for histocompatibility antigens and genes related to diseases caused by disorders of nervous system cells. Modification of the target gene on the chromosome can be carried out using a method described in, for example, Manipulating the Mouse Embryo A Laboratory Manual, Second Edition, Cold Spring Harbor Laboratory Press (1994); Gene Targeting, A Practical Approach, IRL Press at Oxford University Press (1993); Biomanual series 8 Gene Targeting, Preparation of mutant mouse using ES cell, Yodosha (1995) and the like.

Specifically, a genomic gene of the target gene to be modified (e.g., a histocompatibility antigen gene or a disease-related gene) is isolated, and a target vector for homologous recombination of the target gene is produced using the isolated genomic gene. An embryonic stem cell having a modified chromosomal gene can be produced by introducing the thus produced target vector into embryonic stem cells and selecting a cell in which homologous recombination occurred between the target gene and the target vector.

The method for isolating genomic gene of the target gene include a known method described in Molecular Cloning, A Laboratory Manual, Second Edition, Cold Spring Harbor Laboratory Press (1989) or in Current Protocols in Molecular Biology, John Wiley & Sons (1987-1997) and the like. The genomic gene of the target gene can also be isolated, for example, using Genome DNA Library Screening System (manufactured by Genome Systems) or Universal GenomeWalker™ Kits (manufactured by CLONTECH).

The production of the target vector for carrying out homologous recombination of the target gene and efficient selection of a homologous recombinant can be carried out according to the method described in, for example, Gene Targeting, A Practical Approach, IRL Press at Oxford University Press (1993); Biomanual series 8 Gene Targeting, Preparation of mutant mouse using ES cell, Yodosha (1995) and the like. As the target vector, any one of its replacement type and insertion type can be used. As the selection method, the positive selection, promoter selection, negative selection, poly A selection or the like can be used.

The method for selecting the homologous recombinant of interest from the selected cell lines includes the Southern hybridization, PCR and the like for genomic DNA.

Furthermore, the embryonic stem cell is obtained from certain institution and a commercial product thereof can also be purchased. For example, human embryonic stem cells, KhES-1 KhES-2 and KhES-3 are available from Institute for Frontier Medical Sciences, Kyoto University.

Culturing the embryonic stem cells "in the presence of an amnion-derived factor" refers to culturing the embryonic stem cells in a medium comprising at least a factor obtained from the amnion.

The medium used in the culture method of the present invention can be prepared using a medium used for culturing an animal cell as a basal medium. The basal medium is not limited as long as it is available for culturing an animal cell, and include, for example, BME medium, BGJb medium, CMRL 1066 medium, Glasgow MEM medium, Improved MEM Zinc Option medium, IMDM medium, Medium 199 medium, Eagle's MEM medium, αMEM medium, DMEM medium, Ham's medium, RPMI 1640 medium, Fischer's medium and a mixed medium thereof and the like.

Although the medium used in the culture method of the present invention can be a serum-containing medium or a serum-free medium, a serum-free medium is preferable from the viewpoint of assuring the safety of cell transplantation by eliminating heterologous components. Here, a serum-free medium means a medium not containing an unadjusted or unpurified serum, and a medium supplemented with a purified blood-derived component or animal tissue-derived component (e.g., growth factor) is deemed a serum-free medium. Such a serum-free medium includes, for example, a serum-free medium supplemented with an appropriate amount (e.g., 1-20%) of commercially available KNOCKOUT™ SR, a serum-free medium supplemented with insulin and transferrin (e.g., CHO-S-SFM II (manufactured by GIBCO BRL Company), Hybridoma-SFM (manufactured by GIBCO BRL Company), eRDF Dry Powdered Media (manufactured by GIBCOBRL Company), UltraCULTURE™ (manufactured by BioWhittaker Company), UltraDOMA™ (manufactured by BioWhittaker Company), UltraCHO™ (manufactured by BioWhittaker Company), UltraMDCK™ (manufactured by BioWhittaker Company), ITPSG medium (Cytotechnology, 5, S17 (1991)), ITSFn medium (Proc. Natl. Acad. Sci. USA, 77, 457 (1980)), mN3 medium (Mech. Dev., 59, 89 (1996) and the like), a medium supplemented with a cell-derived factor (e.g., a medium supplemented with culture supernatant of multipotent teratocarcinoma cell PSA1 (Proc. Natl. Acad. Sci. USA, 78, 7634 (1981)).

Also, the medium used in the culture method of the present invention may comprise as necessary other components, for example, amino acid, pyruvic acid, 2-mercaptoethanol, cytokines, growth factors and the like, at appropriate concentrations.

The culture vessel used for culturing embryonic stem cells is not limited as long as it is for culturing cells, and include, for example, a flask, a tissue culture flask, a dish, a Petri dish, a tissue culture dish, a multi-dish, a microplate, a micro-well plate, a multi-plate, a multi-well late, a chamber slide, a schale, a tube, a tray, a culture bag, a roller bottle and the like.

Describing the culture method of the present invention more specifically, a means of accomplishing culturing the embryonic stem cells in the presence of an amnion-derived factor can be culturing embryonic stem cells in the presence of the amnion or processed material thereof.

As examples of the amnion or processed material thereof, one derived from a warm-blooded animal, preferably from a mammal, can be used. The mammal includes, for example, mice, rats, guinea pigs, hamsters, rabbits, cats, dogs, sheep, pigs, cattle, horses, goat, monkeys, and humans.

In another aspect, as the amnion or processed material thereof, one derived from the same mammalian species as the embryonic stem cells used in the culture method of the present invention can be used.

The amnion can be prepared by a method known per se. Note that the amnion is preferably collected aseptically by caesarian section. The amnion collected is washed with antibiotic-containing physiological saline to remove blood components and chorion, after which the amnion is cut into pieces of appropriate size and preserved in an appropriate buffer solution. Note that the subject from which the amnion is collected is preferably negative for infections (e.g., hepatitis B, hepatitis C, syphilis, human immunodeficiency virus). The presence or absence of infections can be determined by a method known per se, for example, serological testing.

The processed material of the amnion can be prepared by subjecting the amnion obtained as described above to an optionally chosen treatment. The treatment for preparing the processed material of the amnion includes, for example, cell component removal using EDTA solution, radiation (e.g., γ rays) irradiation, amnion denaturation (e.g., amniocyte immortalization treatment by freeze-thawing), dehydration (e.g., lyophilization), and a combination thereof and the like.

As a preferable processed material of the amnion, the amnion deprived of cells, namely, cell-free tissue can be mentioned. The cell-free tissue can be prepared by a method known per se, for example, by removing cells from the amnion using EDTA and protease. Also, when the amnion used is cell-free tissue, the embryonic stem cells is preferably cultured in contact with the lumenal side of the amnion, on which the amnion-derived active factor is adsorbed in large amounts. In this operation, the cell-free amnion tissue may be pre-treated with a coating agent to enhance its adhesion to the embryonic stem cells. The coating agent includes, for example, collagen, gelatin, poly-L-lysine, fibronectin, and laminin.

Also, as the amnion or processed material thereof, cryopreserved one, for example, lyophilized one, can be used after thawing. Note that the amnion-derived active factor useful for culturing the embryonic stem cells has been confirmed as retaining its activity even when thawed after cryopreservation for a long time. Therefore, the amnion or processed material thereof used in the culture method of the present invention is advantageous in that it can be used even after being preserved with freezing treatment for a long time.

Regarding the amnion or processed material thereof, cryopreservation temperature can be set optionally without limitation, and can, for example, be 0° C. to −100° C., preferably −20° C. to −80° C. Also, the period during which cryopreservation is possible is not subject to limitation, as long as it is a period in which the activity useful for culturing the embryonic stem cells is not completely lost; for example, it can be a period of not more than 3 years, preferably not more than 1 year, more preferably not more than half a year, for preservation at −80° C. Freeze-thawing treatment of the amnion or processed material thereof can be performed by a method known per se.

More specifically, the method for culturing the embryonic stem cells in the presence of the amnion or processed material thereof include a method in which the recovered embryonic stem cells are suspended in an appropriate medium (e.g., a medium produced by adding 5% KNOCKOUT™ SR, 5 ml of 100× non-essential amino acids solution (manufactured by Gibco), 5 ml of 100× pyruvic acid (manufactured by Sigma) and 0.5 ml of $1\times10^{-1}$ M 2-mercaptoethanol to 500 ml of Glasgow MEM medium), the suspension is seeded at a cell density of several tens to several hundreds of cells/cm$^2$ into a culture vessel with which the lumenal side of the cell-free tissue from the amnion is attached as the top, and then the cells are cultured at 37° C. for 3 to 20 days in a stream of several percent, preferably 5%, of carbon dioxide in a $CO_2$ incubator.

In addition, as another means of accomplishing culturing the embryonic stem cells in the presence of the amnion-derived factor, culturing the embryonic stem cells in the presence of amniocytes can be mentioned. From an Example described below, the finding has been obtained that an amnion-derived active factor useful for culturing the embryonic stem cell is adsorbed in large amounts on the lumenal side of cell-free amnion tissue. This strongly suggests that such an active factor may be produced by amniocyte.

"Amniocyte" refers to a cell present in the amnion; for example, primary culture cell prepared from epithelial cell and stromal cell of an amnion, cell line derived from the primary culture cell and the like can be mentioned. An amniocyte that produce an amnion-derived active factor useful for culturing the embryonic stem cells (e.g., a factor having differentiation-inducing activity and/or growth activity of the embryonic stem cells) can be prepared by the method described below.

As examples of the amniocyte, a cell derived from a warm-blooded animal, preferably from a mammal described above, can be used.

In another aspect, as the amniocyte, a cell derived from the same mammalian species as the embryonic stem cell used in the culture method of the present invention can be used.

Culturing the embryonic stem cells in the presence of the amniocyte can be performed while the embryonic stem cells and the amniocytes are in contact with each other, or not in contact with each other, preferably in contact with each other. Culturing the embryonic stem cells using the amniocyte can be performed under the same conditions as the culturing using the amnion or processed material thereof, except for the use of the amniocyte.

Furthermore, as another means of accomplishing culturing the embryonic stem cells in the presence of the amnion-derived factor, culturing the embryonic stem cells using a medium supplemented with a solubilized extract comprising the amnion-derived factor can be mentioned. From the Example described below, the finding has been obtained that an amnion-derived factor useful for culturing the embryonic stem cells is adsorbed or bound in large amounts to the lumenal side of cell-free amnion tissue. This suggests that such an amnion-derived factor is a hydrophobic substance or an extracellular matrix-binding substance. Therefore, this amnion-derived factor can be extracted by a method known per se, such as a treatment with an organic solvent, a solubilizer (e.g., surfactant), a polyanionic polymer (e.g., heparin) or the like, or an extracellular matrix degradation treatment (e.g., treatment with heparinase and the like).

An amnion-derived factor can be extracted by, for example, treating the amnion or processed material thereof, or the amniocyte, with an organic solvent and the like, as described above. Note that the amnion-derived factor need not be purified, and can be used in the form of an unpurified fraction in the culture method of the present invention. Note that whether or not the extracted fraction has an activity useful for culturing the embryonic stem cells can be determined by using it for culturing the embryonic stem cells.

The cell culture obtained by the culture method of the present invention is also provided by the present invention. The cell culture of the present invention preferably does not substantially comprise a component derived from a mammal other than the mammal from which the embryonic stem cells are derived. In addition, the cell culture of the present invention has advantages, including unlikelihood of graft rejection reactions and high safety in transplantation, because an amnion component is used in the culturing.

In one embodiment, the culture method of the present invention can be a method of inducing differentiation of the embryonic stem cells. The differentiation-inducing method of the present invention is not subject to limitation, as long as it causes differentiation of the embryonic stem cells; for example, the embryonic stem cells can be differentiated into ectodermal cells. The ectodermal cells include, for example, nervous system cells, epidermal cells, sensory organ cells, pigment cells, and neural crest-derived mesenchymal cells.

In the differentiation-inducing method of the present invention, to further improve the differentiation efficiency into nervous system cells, a known substance of inducing differentiation into ectodermal cells can be used in combination. As examples of such a differentiation inducing substance, the Wnt inhibitor (Nature Biotechnology, 20, 1240-1245 (2002)) can be mentioned, in addition to the substance of inducing differentiation into nervous system cells described below.

Preferably, in the differentiation-inducing method of the present invention, differentiation of the embryonic stem cells into the nervous system cells can be induced.

In addition, in the differentiation-inducing method of the present invention, the embryonic stem cells are preferably cultured in a serum-free medium from the viewpoint of accomplishing specific differentiation induction.

Furthermore, in the differentiation-inducing method of the present invention, to further improve the differentiation efficiency into nervous system cells, a known substance of inducing differentiation into nervous system cells can be used in combination. As examples of such a differentiation inducing substance, NGF (Biochem. Biophys. Res. Commun., 199, 552 (1994)), retinoic acid (Dev. Biol., 168, 342 (1995)); J. Neurosci., 16, 1056 (1996)), FGF (Genes & Development, 15, 3023-8 (2003)), BMP inhibitory factor (Nature, 376, 333-336 (1995)), and IGF (Genes & Development, 15, 3023-8 (2003)) can be mentioned. Of course, differentiation into nervous system cells is possible even in the absence of these differentiation inducing substances.

A feature of nervous system cells differentiation-induced by the method of the present invention resides in that the ratio of Sox-1-positive colonies is substantially about 100%. Another feature of the differentiation-inducing method of the present invention resides in that not less than about 80%, for example, about 80% to 90%, of nervous system cells in the Sox-1-positive colonies are NCAM-positive cells.

Specifically, the nervous system cell which can be differentiation-induced by the method of the present invention includes, for example, neural stem cell, neuron, cell of neural tube, cell of neural crest and the like.

The neuron refers to cell which functions to receive a stimulus from other neurons or stimulus receptor cells and transmit the stimulus to another neurons, muscle or glandular cells. The neuron is classified based on the difference in the neurotransmitter produced by the neurons, for example, based on the difference in the secreted neurotransmitter and the like. Examples of neurons classified by these neurotransmitters include dopamine-secreting neurons, acetylcholine-secreting neurons, serotonin-secreting neurons, noradrenaline-secreting neurons, adrenaline-secreting neurons, glutamate-secreting neurons and the like. The dopamine-secreting neurons, the noradrenaline-secreting neurons and the adrenaline-secreting neurons are generally referred to as catecholamine-secreting neurons.

A feature of neurons differentiation-induced by the method of the present invention resides in that the ratio of tyrosine hydroxylase (TH)-positive colonies is not less than about 50%, for example, about 50% to about 70%. Another feature of the differentiation-inducing method of the present invention resides in that about 30% of neurons in the TH-positive colonies are TH-positive cells.

The differentiation-inducing method of the present invention can be used for differentiation into the neurons. It can be used for differentiation into, preferably, the catecholamine-secreting neurons (e.g., the dopamine-secreting neurons) of the neurons.

The neural stem cell refers to cell having an ability to be capable of differentiating into a neuron, an astrocyte and an oligodendrocyte and having self-replicating ability, and it functions to supply a neuron, an astrocyte and an oligodendrocyte in the brain. Accordingly, methods of confirming that the cell is the neural stem cell include a method in which the cell is acutally transplanted into the brain and its differentiation ability is confirmed and a method in which inducing differentiation of the neural stem cell into a neuron, an astrocyte and an oligodendrocyte is confirmed in vitro (Mol. Cell. Neuro Science, 8, 389 (1997); Science, 283, 534 (1999)). Also, the neural stem cell having such a function can be stained with an anti-nestin antibody which recognizes a cytoskeletal protein nestin whose expression in a nerve precursor cell has been confirmed (Science, 276, 66 (1997)). Accordingly, the neural stem cell can be confirmed by staining with the anti-nestin antibody.

The cell culture obtained by the differentiation-inducing method of the present invention is also provided by the present invention. The cell culture has the same features as those of the above-described cell culture obtained by the culture method of the present invention.

The cell obtained by the differentiation-regulating method of the present invention can be used as a therapeutic agent for diseases caused by the disorder of nervous system cells, or for supplementing with nervous system cells in neural damage due to other causes, or the like. The disease caused by the disorder of nervous system cells include Parkinson disease, Huntington disease, Alzheimer disease, ischemic cerebral disease, epilepsy, brain injury, vertebral injury, motor neuron disease, neurodegenerative disease, pigmentary retinal dystrophy, cochlear hearing loss, multiple sclerosis, amyotrophic lateral sclerosis, a disease due to a neurotoxin damage and the like.

Furthermore, when the cells obtained by the differentiation-regulating method of the present invention are used, for example, as a therapeutic agent for diseases caused by the disorder of nervous system cells, it is preferred that the cells are transplanted into a subject after increasing purity of the cells.

Any one of the already known methods for separating and purifying cells can be used as the method for increasing purity of cells. Examples include a method using a flow cytometer (see, e.g., Antibodies—A Laboratory Manual, Cold Spring Harbor Laboratory (1988); Monoclonal Antibodies: principles and practice, Third Edition, Acad. Press (1993); Int. Immunol., 10, 275 (1998)), Panning method (see, e.g., Monoclonal Antibodies: principles and practice, Third Edition, Acad. Press (1993); Antibody Engineering, A Practical Approach, IRL Pressat Oxford University Press (1996); J. Immunol., 141, 2797 (1988)) and a cell fractionation method using density difference of sucrose concentration (see, e.g., Techniques of Tissue Culture (Third Edition), Asakura Shoten (1996)).

The method for increasing purity of differentiated cells of the present invention comprises culturing the nervous system cells, especially neurons, obtained by inducing differentiation of the embryonic stem cells as described above, in a medium comprising an anticancer agent. Since cells under an undifferentiated state can be removed by this step, and differentiated cells can be obtained with further higher purity, so that it becomes more suitable as a pharmaceutical agent. That is, by the treatment with an anticancer agent, cells other than the differentiated cells of interest, such as undifferentiated cells, can be removed.

Here, the anticancer agents include mitomycin C, 5-fluorouracil, adriamycin, ara-C, methotrexate and the like. It is preferable to use these anticancer agents at a concentration which shows stronger cytotoxicity on undifferentiated cells than that on differentiated cells. Specifically, the optimum concentration can be determined by carrying out culturing with these anticancer agents according to the method described above, such as a method in which culturing is carried out at 37° C. for several hours, preferably 2 hours, in a stream of 5% carbon dioxide in a $CO_2$ incubator, using a medium comprising any of these anticancer agents at a concentration of 1/100 to 1 equivalent of the concentration used in the living body described in the Pharmacopoeia of Japan.

Any medium can be used in this method, so long as it is capable of culturing differentiation-induced cells. Specifically, the medium described above and the like can be mentioned.

In addition, in the transplantation medical treatment, rejection due to difference in the histocompatibility antigens sometimes causes a problem, but this problem can be resolved by using the embryonic stem cell into which the nucleus of a somatic cell has been transplanted, or the embryonic stem cell in which a gene on the chromosome has been modified.

Furthermore, a neuron of a somatic cell-donated individual can be obtained by carrying out induction of the differentiation using the embryonic stem cell into which the nucleus of a somatic cell has been transplanted. Such a cell of individual is useful not only as a transplantation medical treatment of the cell itself but also as a diagnosing material for judging whether or not an existing drug is effective for the individual. Also, since sensitivities to oxidation stress and aging can be judged by culturing a differentiation-induced cell for a prolonged period of time, risk of individual for a disease such as a neurodegenerative disease can be evaluated by comparing its function and life with those of a cell derived from other individual, and the evaluation data are useful for providing an effective method for preventing a disease which is diagnosed as high in its future morbidity rate.

Neurons differentiation-induced from the embryonic stem cells can be transplanted to diseased parts of the body of a patient by a method known per se (see, e.g., Nature Neuroscience, 2, 1137 (1999)).

In another embodiment, the culture method of the present invention can be a method of growing the embryonic stem cells. The growing method of the present invention is not subject to limitation, as long as it causes an increase in the number of embryonic stem cells, and it can preferably be a method that causes an increase in the number of embryonic stem cells while maintaining the undifferentiated state.

In the growing method of the present invention, the embryonic stem cells are preferably cultured in a serum-free medium to maintain the undifferentiated state.

In the growing method of the present invention, a differentiation suppressing substance can be used in combination to maintain the undifferentiated state. Such a differentiation suppressing substance includes, for example, LIF (leukaemia inhibitory factor) (Development, 110, 1341 (1990); Dev. Biol., 141, 344 (1990)) and the GSK3 inhibitor (Nature Medicine, 10, 55-63 (2003)). Of course, it is possible to maintain the undifferentiated state even in the absence of these differentiation suppressing substances.

The growing method of the present invention causes an increase in the number of embryonic stem cells while in the undifferentiated state, and in turn makes it possible to obtain a greater number of cells for transplantation by using in combination with the differentiation-inducing method of the present invention.

The cell culture obtained by the growing method of the present invention is also provided by the present invention. Note that the cell culture has the same features as those of the above-described cell culture obtained by the culture method of the present invention.

The present invention also provides a method of screening an amnion-derived factor which is useful for culturing the embryonic stem cells, for example, a factor having the differentiation-inducing activity or growth activity of the embryonic stem cells, which comprises using the activity as an index, and the amnion-derived factor which can be obtained by the method.

An amnion-derived active factor can be purified with, for example, differentiation-inducing activity or growth activity of the embryonic stem cells with cell-free amnion tissue added as the starting material to the medium, as an index. The purification methods includes, for example, solvent extraction, salting-out with ammonium sulfate and the like, desalinization, organic solvent precipitation, anion exchange chromatography, cation exchange chromatography, hydrophobicity chromatography, gel filtration using a molecular sieve, affinity chromatography, chromatofocusing, an electrophoresis such as isoelectric focusing, or a combination of these methods.

In addition, the amnion-derived active factor can be obtained from an amniocyte using an expression cloning method (Molecular Cloning, Second Edition, Current Protocols in Molecular Biology, Third Edition, Acad. Press (1993); Antibody Engineering: A Practical Approach, IRL Press at Oxford University Press (1996)).

Specifically, cDNA is prepared from an amniocyte and the cDNA is inserted into downstream of the promoter of an appropriate expression vector to prepare a recombinant vector, and then a cDNA library is prepared. Transformants which produce gene products produced by the amniocyte are obtained by introducing the recombinant vector into a host cell suitable for the expression vector, and a transformant which produces a gene product having the differentiation-inducing activity or growth activity is selected therefrom. A factor having the differentiation-inducing activity or growth activity can be obtained by determining the gene sequence encoded by the cDNA introduced into the selected transformant.

As a host cell used in the screening method of the present invention, any cells which does not have an activity of inducing differentiation of embryonic stem cells into nervous system cells can be used. For example, such cells include CHO cell, MDCK cell, rat fibroblast 3Y1 and COS cell.

As the cell used for preparation of cDNA, the above-described amniocyte having differentiation-inducing activity or growth activity of the embryonic stem cells is used.

As the cell to be used in the preparation of cDNA, the above-described amniocyte having the differentiation-inducing activity or growth activity of the embryonic stem cells is used.

The cDNA libraly can be prepared by the methods known per se. The thus produced cDNA library may be used as such, but, in order to concentrate the target gene, a cDNA library produced by carrying out a subtraction method (Proc. Natl. Acad. Sci. USA, 85, 5783 (1988)) using mRNA of a cell which does not have the differentiation-inducing activity or growth activity of the embryonic stem cells can also be used.

As the introduction method of the recombinant vector into the host cell, any method can be used, so long as it is a method for introducing DNA into an animal cell. Examples include electroporation method, calcium phosphate method and lipofection method.

A gene product encoded by introduced cDNA can be expressed by culturing the transformant obtained as described above in a medium. Method for culturing the transformant in the culture can be carried out according to conventional methods used for culturing a host. For example, As the medium, RPMI1640 medium, αMEM medium, DMEM medium, 199 medium and medium supplementing these medium with fetal calf serum and the like, and the like can be used. The culturing is normally carried out under conditions such as pH 6-8, at 30-40° C. in the presence of 5% $CO_2$ for 1-7 days. Additionally, antibiotics such as kanamycin and penicillin may be optionally added through a period of culturing.

In the screening method of the present invention, a transformant which produces a gene product having the differentiation-inducing activity or growth activity of the embryonic stem cells can be selected by carrying out coculture of the embryonic stem cells and the transformant. Isolation of cDNA introduced into the selected transformant, and determination of gene sequence of the isolated cDNA can be carried out by the methods known per se.

The screening method of the present invention is useful for enabling screening of an amnion-derived active factor which is useful for culturing embryonic stem cells. The amnion-derived factor which is obtained by the screening method is also useful for additives in a culture medium for embryonic stem cells.

The present invention further provides an agent of culturing the embryonic stem cells, which comprises an amnion-derived factor.

The culture agent of the present invention is not subject to limitation, as long as it is capable of directly or indirectly providing an amnion-derived factor for culturing the embryonic stem cells.

In one embodiment, the culture agent of the present invention is a biological tangible entity to which an amnion-derived factor adheres or a solution containing an amnion-derived factor. The biological tangible entity to which an amnion-derived factor adheres is not subject to limitation, as long as it is an organism-derived material (e.g., cells, tissue) to which an amnion-derived factor adheres; for example, the amnion or processed material thereof (e.g., cell-free tissue), and amniocytes can be mentioned. The solution containing an amnion-derived factor includes, for example, organic solvent extract, solubilizer (e.g., surfactant) extract, polyanion extract, and enzymolytic extract of extracellular matrix. Additionally, when the amnion-derived active factor has been isolated, it is also possible to provide a culture agent substantially consisting of the active factor.

In another embodiment, the culture agent of the present invention is provided in the form of a combination of a biological tangible entity to which an amnion-derived factor adheres or an extract containing an amnion-derived factor, and a substrate. Specifically, this culture agent is provided in a form wherein any of the above-described various forms of amnion-derived factor adheres or is immobilized to, or coated on, the substrate, or is impregnated in the substrate. The substrate is not subject to limitation, as long as it is capable of adhering, immobilizing, or coating the tangible entity, or of impregnating the liquid; for example, culture sheets (e.g., culture inserts such as porous membranes), beads, hollow fibers, and polymeric gels can be mentioned in addition to the above-described culture vessels.

Furthermore, the culture agent of the present invention may be provided in a cryopreserved form, for example, in a lyophilized form. Note that an amnion-derived active factor useful for culturing the embryonic stem cells has been confirmed as retaining its activity even when thawed after cryopreservation for a long time. Therefore, the culture agent of the present invention is advantageous in that it can be used even after long-term preservation with freezing treatment.

Regarding the culture agent of the present invention, cryopreservation temperature can be set optionally without limitation, and can, for example, be 0° C. to −100° C., preferably −20° C. to −80° C. Additionally, the period in which cryopreservation is possible is not subject to limitation, as long as it is a period in which the activity useful for culturing the embryonic stem cells is not completely lost; for example, it can be a period of not more than 3 years, preferably not more than 1 year, more preferably not more than half a year, at −80° C.

In one embodiment, the culture agent of the present invention can be an agent of inducing differentiation of the embryonic stem cells, which comprises the amnion-derived factor having differentiation-inducing activity of the embryonic stem cells. The differentiation-inducing agent of the present invention can further comprise the above-described substance of inducing differentiation into ectodermal cells, preferably a substance of inducing differentiation into nervous system cells.

In another embodiment, the culture agent of the present invention can be an agent of growing the embryonic stem cells, which comprises an amnion-derived factor having growth activity of the embryonic stem cells. The growing agent of the present invention can further comprise the above-described differentiation suppressing substance.

The culture agent of the present invention is useful for culturing the embryonic stem cells, for example, for inducing the differentiation of embryonic stem cells, and/or for growing the embryonic stem cells, and the like.

The present invention also provides a kit of culturing the embryonic stem cells, which comprises (i) the culture agent of the present invention, and (ii) a manual stating that the kit should be used, or can be used, for culturing the embryonic stem cells.

In the kit of the present invention, when the culture agent is not provided in a form adhering to, or immobilized or coated on, the substrate, or in a form impregnated in a substrate, such a substrate may be included in the kit of the present invention.

The culture kit of the present invention can further comprises a medium for embryonic stem cells, a medium additive and the like, in addition to those mentioned above.

In one embodiment, the culture kit of the present invention can be a kit of inducing differentiation of the embryonic stem cells, which comprises (i) the culture agent of the present invention, and (ii) a manual stating that the kit should be used, or can be used, for inducing differentiation of the embryonic stem cells into ectodermal cells, and/or an antibody against an ectodermal cell marker.

The antibody against an ectodermal cell marker is not subject to limitation, as long as it is an antibody capable of confirming the differentiation of embryonic stem cells into ectodermal cells; for example, it can be an antibody against a nervous system cell marker. The antibodies against a nervous system cell marker is not subject to limitation, as long as it is an antibody capable of confirming the differentiation of embryonic stem cells into nervous system cells; for example, an antibody against NCAM, TuJ1, tyrosine hydroxylase (TH), serotonin, nestin, MAP2, MAP2ab, NeuN, GABA, glutamate and ChAT can be mentioned.

In addition, as the antibody against ectodermal cell marker, antibodies against epidermal cell markers (e.g., cytokeratin), sensory organ cell markers (e.g., RPE, rhodopsin), pigment cell markers (e.g., TRP-1), nerve crest-derived mesenchymal cells (e.g., SMA) and the like can also be mentioned.

The antibody contained in the kit of the present invention may be a polyclonal antibody or monoclonal antibody, and can be prepared by a well-known immunological technique. This antibody is not only a complete antibody molecule, but also any fragment as long as it has an antigen-binding site (CDR) for the marker, and is exemplified by Fab, $F(ab')_{21}$ ScFv, minibody, and the like. Furthermore, the antibody of the present invention may be labeled with detectable labeling substance (e.g., fluorescent substance).

For example, a polyclonal antibody can be obtained by giving the marker [may be prepared as a complex cross-linked with a carrier protein such as bovine serum albumin or KLH (Keyhole Limpet Hemocyanin), if necessary], along with a commercially available adjuvant (e.g., complete or incomplete Freund's adjuvant), to an animal by subcutaneous or intraperitoneal administration about 2 to 4 times at intervals of 2 to 3 weeks (the antibody titer of serum separated from drawn blood determined by a commonly known antigen-antibody reaction, and its elevation confirmed in advance), collecting whole blood about 3 to about 10 days after final immunization, and purifying the antiserum. Animals to be administered with the antigen include mammals such as rats, mice, rabbits, goat, guinea pigs and hamsters.

A monoclonal antibody can also be prepared by a cell fusion method. For example, a mouse is given this factor, along with a commercially available adjuvant, 2 to 4 times by subcutaneous or intraperitoneal administration, its spleen or lymph node is collected about 3 days after final administration, and leukocytes are separated. These leukocytes are fused with myeloma cells (e.g., NS-1, P3X63Ag8, etc.) to yield a hybridoma that produces a monoclonal antibody against this antigen. The cell fusion may be achieved by the PEG method or the voltage pulsation method. A hybridoma that produces the desired monoclonal antibody can be selected by detecting in the culture supernatant an antibody that specifically binds to an antigen using well-known EIA, RIA, or the like. Cultivation of a hybridoma that produces a monoclonal antibody can be conducted in vitro, or in vivo in mice or rats, preferably in ascites fluid of mouse, and the resulting antibody can be obtained from a hybridoma culture supernatant or animal ascites fluid, respectively.

The differentiation-inducing kit of the present invention can preferably be a kit for inducing differentiation into nervous system cells. In this case, the kit can comprise an antibody against a nervous system cell marker.

In Addition, the differentiation inducing kit of the present invention can further comprise an antibody against an embryonic stem cell marker described below, in addition to the above-described substance of inducing differentiation into ectodermal cells, preferably the substance of inducing differentiation into nervous system cells.

The kit of the present invention can further comprise a means capable of detecting an antibody against a marker. As examples of the means capable of detecting an antibody against a marker, labeling substances (e.g., fluorescent substances, luminescent substances), secondary antibodies against markers and the like can be mentioned.

In another embodiment, the culture kit of the present invention can be a kit of growing the embryonic stem cells, which comprises (i) the culture agent of the present invention, and (ii) a manual stating that the kit should be used, or can be used, for growing the embryonic stem cells, and/or an antibody against an embryonic stem cell marker.

The antibody against an embryonic stem cell marker is not subject to limitation, as long as it is an antibody capable of confirming maintenance state of the embryonic stem cell; for example, antibodies against SSEA-1, alkaline phosphatase, and Nanog can be mentioned.

The growing kit of the present invention can further comprise the above-described substance of suppressing differentiation of the embryonic stem cells.

The kit of the present invention is useful for enabling the provision of a convenient means for culturing embryonic stem cells, particularly for inducing and/or growing the embryonic stem cells.

The present invention also relates to a method of preparing an amniocyte useful for culturing the embryonic stem cells, and the amniocytes prepared by the method. The preparation method of the present invention comprises preparing the amniocyte having an activity useful for culturing the embryonic stem cells, for example, differentiation-inducing activity and/or growth activity of the embryonic stem cells, with the activity as an index.

The amniocyte can be prepared by methods known per se (see, Current Protocols in Cell Biology, John Wiley & Sons, Inc. (2001); Separation and Cultivation of Functional Cell, Maruzen Syoten (1987)). For example, a primary amniocyte can be prepared by dissociating cells from an amnion with EDTA, protease and the like, and recovering the cells.

In addition, a cell line of amniocyte can be established by the methods known per se (see, Current Protocols in Cell Biology, John Wiley & Sons, Inc. (2001); Separation and Cultivation of Functional Cell, Maruzen Shoten (1987)). For example, the establishing methods include treatment by virus, chemical carcinogen or irradiation, and a method for isolating a cell acquiring unlimited growth capacity from primary culture cells.

Whether or not the established cell line has the activity which is useful for culturing the embryonic stem cells, for example, the differentiation-inducing activity and/or growth activity of the embryonic stem cells is confirmed by culturing the embryonic stem cells in the presence of the cell line.

The amniocyte prepared by this method are useful for culturing the embryonic stem cells, for example, for inducing differentiation of, and/or growing the embryonic stem cell.

EXAMPLES

The present invention is hereinafter described in more detail by means of the following examples, which, however, merely show illustration and are not to be construed as limiting scope of the present invention.

Example 1

Preparation of Human Amnion Tissue

After consent in writing with regard to the use of her placenta was obtained from a pregnant woman with no systemic complications who was scheduled to undergo caesarian section and determined to be negative for infections by serological testing, the amnion was aseptically collected from the placenta extirpated in caesarian section. The amnion collected was washed with antibiotic-containing physiological saline to remove blood components and chorion, after which the amnion was cut into pieces of appropriate size and rapidly frozen in antibiotic-supplemented 50% glycerol/DMEM in a deep freezer, after which they were preserved in a dedicated refrigerator at −80° C.

Example 2

Preparation of Feed Plate of Cell-free Tissue from Amnion

After the amnion cryopreserved (7 months) was thawed, it was reacted in 0.02% EDTA at 37° C. for 2 hours, and the cells were removed from the amnion to prepare cell-free amnion tissue. Next, a porous membrane culture insert was inserted into a 6-well plate (diameter of each well: 3.5 cm), and the cell-free amnion tissue was mounted on the porous membrane culture insert with the luminal side thereof up. Next, to promote ES cell adhesion, the cell-free amnion tissue was pre-coated with gelatin or fibronectin.

Example 3

Culture of ES Cells in the Presence of Amnion-derived Factor

In this Example, mouse ES cells wherein GFP (green fluorescent protein) was knocked in the nerve marker Sox1 gene by homologous recombination (hereinafter abbreviated as Sox1/GFP-mES cells as necessary; see Nature Biotechnology, Vol. 21: 183-186 (2003)) were used as ES cells. For maintenance culture of the ES cells, an ordinary culture method using feeder-free cells were employed by supplementing with 1% fetal bovine serum, 10% KSR (Knockout Serum Replacement) and LIF (see Neuron, Vol. 28: 31-40 (2000)). After an ES cell colony was rendered single cells by trypsin/EDTA treatment, they were seeded onto the cell-free tissue prepared in Examples 1 and 2 above, and cultured in a differentiation medium (GMEM, 10% KSR, 2 mM glutamic acid, 1 mM pyruvic acid, 0.1 mM non-essential amino acid mixed solution, 0.1 mM 2-mercaptoethanol; Neuron, Vol. 28: 31-40 (2000)). Note that the ES cells were seeded at a density of 1000-2000 cells/well, and incubated at 37° C. in 5% $CO_2$ for 7 days.

As a result, after 7 days of culture, colonization from each ES cell was confirmed. In the meantime, when the same experiment was performed in the absence of cell-free amnion tissue, colonization from each ES cell was confirmed but colony size was inferior to that obtained by culture in the presence of cell-free tissue. This indicates that cell-free amnion tissue has growth activity of ES cell.

In addition, after 7 days of culture, the GFP signal, which is a nerve-specific reporter, was observed in 100% of the ES cell colonies. Furthermore, about 80 to 90% of these cells in the colonies were found to be positive for NCAM (pan-nerve marker) by the fluorescent antibody method using an anti-NCAM antibody (manufactured by Chemicon). This indicates that cell-free amnion tissue has an activity to induce the differentiation of ES cells into ectodermal cells, particularly into nervous system cells.

Hence, cell-free amnion tissue was demonstrated to have ES cell growth activity/differentiation-inducing activity, and to be useful for culturing ES cells.

Example 4

Induction of Differentiation of ES Cells into Tyrosine Hydroxylase (TH)-positive Cells by Culturing in the Presence of Cell-free Amnion Tissue In this Example, EB5 cells (Nature Genet., 24, 372 (2000)), which are mouse ES cells (derived from E14), were used as ES cells. Also, ES cell differentiation induction was performed in the same manner as Example 3. After the ES cells were cultured on cell-free amnion tissue for 11 days, colonies of ES cells were isolated by collagenase treatment. After the isolated ES cell colonies were cultured in a differentiation medium (see Example 1) on a poly-D-lysine/laminin-coated culture plate for 2 days, they were fixed and examined by the fluorescent antibody method. The antibodies used were an anti-TuJ1 antibody (manufactured by Babco) and an anti-TH antibody (manufactured by Chemicon).

As a result, 98% of the ES cell colonies were positive for TuJ1, a neuron marker. Also, 54 to 64% of the ES cell colonies were positive for TH, a catecholamine-secreting neuron marker (also used as a dopamine-secreting neuron marker). Furthermore, in the TH-positive colonies, about 30% of the cells were positive for TH.

Hence, it was revealed that by culturing in the presence of an amnion-derived factor, nervous system cells, particularly TH-positive cells, can be efficiently differentiation-induced from ES cells.

INDUSTRIAL APPLICABILITY

According to the present invention, because the risk of transplantation of cells obtained by culturing embryonic stem cells can be lessened to the risk level of homologous transplantation, the present invention is useful from the viewpoint of clinical applications of cell transplantation. Also, because the amnion has advantages, including unlikelihood of graft rejection reactions, easy availability, and much experience with clinical use and hence high safety, the present invention is advantageous in that it is highly practical. Furthermore, according to the present invention, because it is possible to efficiently induce the differentiation of embryonic stem cells into nervous system cells while retaining these features, the present invention is useful from the viewpoint of treatment for nerve degenerative diseases such as Parkinson's disease.

According to the present invention, the risk of transplantation of cells obtained by culturing embryonic stem cells can be lessened to the risk level of homologous transplantation. Also, because the amnion has advantages, including unlikelihood of graft rejection reactions, easy availability, and much experience with clinical use and hence high safety, the present invention, which comprises using an amnion-derived factor, is advantageous in that it is highly practical. Furthermore, according to the present invention, it is possible to efficiently induce the differentiation of embryonic stem cells to nervous system cells while retaining these features.

This application is based on a patent application No. 2004-158421 filed in Japan (filing date: May 27, 2004), the contents of which are entirely incorporated herein.

The invention claimed is:

1. A method of inducing differentiation of mammalian embryonic stem cells into nervous system cells, which comprises culturing the embryonic stem cells in the presence of cell-free amnion tissue in a serum-free medium to induce differentiation of the embryonic stem cells into nervous system cells.

2. The method of claim 1, wherein both the cell-free amnion tissue and embryonic stem cells are derived from the same mammalian species.

3. The method of claim 2, wherein the cell-free amnion tissue is derived from a human.

4. The method of claim 1, wherein the nervous system cells are catecholamine-secreting neurons.

5. The method of claim 1, wherein the nervous system cells are tyrosine hydroxylase-positive cells.

* * * * *